United States Patent
Kawanishi et al.

(10) Patent No.: US 10,987,079 B2
(45) Date of Patent: Apr. 27, 2021

(54) RADIATION IMAGING SYSTEM, METHOD OF CONTROLLING THE SAME, CONTROL APPARATUS, AND STORAGE MEDIUM

(71) Applicant: CANON KABUSHIKI KAISHA, Tokyo (JP)

(72) Inventors: Tomohiro Kawanishi, Tachikawa (JP); Yuichi Nishii, Kawasaki (JP); Hikaru Tanaka, Kawasaki (JP); Kenta Endoh, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 62 days.

(21) Appl. No.: 16/379,954

(22) Filed: Apr. 10, 2019

(65) Prior Publication Data

US 2019/0231295 A1 Aug. 1, 2019

Related U.S. Application Data

(63) Continuation of application No. PCT/JP2017/035485, filed on Sep. 29, 2017.

(30) Foreign Application Priority Data

Oct. 14, 2016 (JP) .............................. JP2016-203040

(51) Int. Cl.
A61B 6/00 (2006.01)
(52) U.S. Cl.
CPC ................. *A61B 6/54* (2013.01); *A61B 6/00* (2013.01); *A61B 6/44* (2013.01); *A61B 6/566* (2013.01)

(58) Field of Classification Search
CPC ................ A61B 6/54; A61B 6/00; A61B 6/44
See application file for complete search history.

(56) References Cited

U.S. PATENT DOCUMENTS

2009/0022276 A1* 1/2009 Ohara .................. A61B 6/4233
378/101
2013/0229280 A1 9/2013 Nishii

FOREIGN PATENT DOCUMENTS

| JP | 2011177347 A | 9/2011 |
| JP | 2011177348 A | 9/2011 |
| JP | 2015062468 A | 4/2015 |
| WO | 2010073894 A | 7/2010 |

* cited by examiner

*Primary Examiner* — Hugh Maupin
(74) *Attorney, Agent, or Firm* — Carter, DeLuca & Farrell LLP

(57) ABSTRACT

A radiation imaging system includes a plurality of imaging apparatuses configured to generate images based on radiation emitted from radiation generating apparatuses configured to perform radiation irradiation and a control apparatus configured to communicate with the plurality of the imaging apparatuses. The control apparatus comprises: an obtainment unit configured to obtain imaging information from each of the plurality of imaging apparatuses, a selection unit configured to select one imaging apparatus from the plurality of imaging apparatuses based on the imaging information obtained by the obtainment unit, and an image obtainment unit configured to obtain an image from the imaging apparatus selected by the selection unit, and the control apparatus further comprises a setting unit configured to set an imaging apparatus from which imaging information is obtained by the obtainment unit.

17 Claims, 9 Drawing Sheets

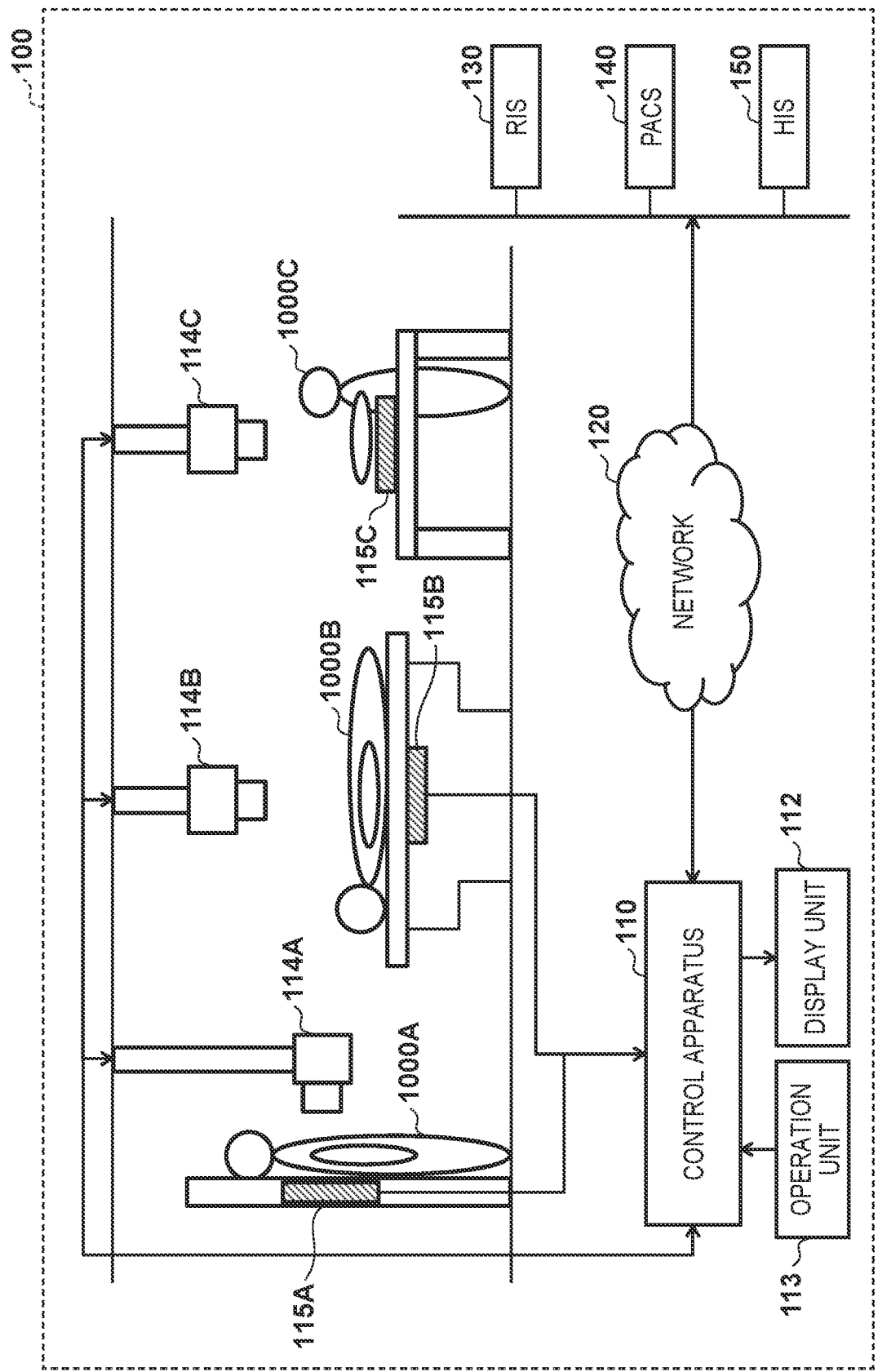

RADIATION IMAGING SYSTEM, METHOD OF CONTROLLING THE SAME, CONTROL APPARATUS, AND STORAGE MEDIUM

CROSS-REFERENCE TO RELATED APPLICATIONS

This application is a Continuation of International Patent Application No. PCT/JP2017/035485, filed Sep. 29, 2017, which claims the benefit of Japanese Patent Application No. 2016-203040, filed Oct. 14, 2016, both of which are hereby incorporated by reference herein in their entirety.

BACKGROUND OF THE INVENTION

Field of the Invention

The present invention relates to a radiation imaging system, a method of controlling the same, a control apparatus, and a storage medium.

Background Art

In recent years, due to digitization of radiation imaging systems, a radiation imaging system that causes a radiation source to irradiate a radiation detector with radiation via an object, causes the radiation detector to generate a digital radiation image, and allows the image to be confirmed immediately after the radiation imaging has become popular. Along with this, the workflow has greatly improved compared to that of radiation imaging performed by using a conventional film or CR (Computed Radiography) apparatus. On the other hand, in contrast to radiation imaging performed by using a conventional film or CR apparatus, a radiation detector needs to be selected and used since radiation imaging will be performed in communication with the radiation detector to be used for imaging.

PTL1 discloses a radiation imaging system that can perform radiation imaging under the same workflow as in a case in which a conventional film is used by setting a plurality of radiation detectors to be in an imaging enabled state in advance so that radiation imaging can be executed when any radiation detector is irradiated with radiation. The arrangement of PTL1 is set in a state in which a radiation image from every radiation detector can be captured.

CITATION LIST

Patent Literature

PTL 1: Japanese Patent Laid-Open No. 2011-177348

However, in the radiation imaging system disclosed in PTL1, all of the plurality of radiation detectors registered in the radiation imaging system need to be set to an imaging enabled state to perform imaging. This may unwantedly degrade the imaging efficiency.

The present invention provides a technique that allows radiation imaging to be performed efficiently even in a case in which not every radiation detector is set to an imaging enabled state.

SUMMARY OF THE INVENTION

A radiation imaging system according to the present invention includes the following arrangement. That is, a radiation imaging system that includes a plurality of imaging apparatuses configured to generate images based on radiation emitted from radiation generating apparatuses configured to perform radiation irradiation and a control apparatus configured to communicate with the plurality of the imaging apparatuses, wherein the control apparatus comprises an obtainment unit configured to obtain imaging information from each of the plurality of imaging apparatuses, a selection unit configured to select one imaging apparatus from the plurality of imaging apparatuses based on the imaging information obtained by the obtainment unit, and an image obtainment unit configured to obtain an image from the imaging apparatus selected by the selection unit, and the control apparatus comprises a setting unit configured to set an imaging apparatus from which imaging information is obtained by the obtainment unit.

Further features of the present invention will become apparent from the following description of exemplary embodiments with reference to the attached drawings.

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 1 is a view showing a schematic arrangement of a radiation imaging system;

DESCRIPTION OF THE EMBODIMENTS

Figure 2A:
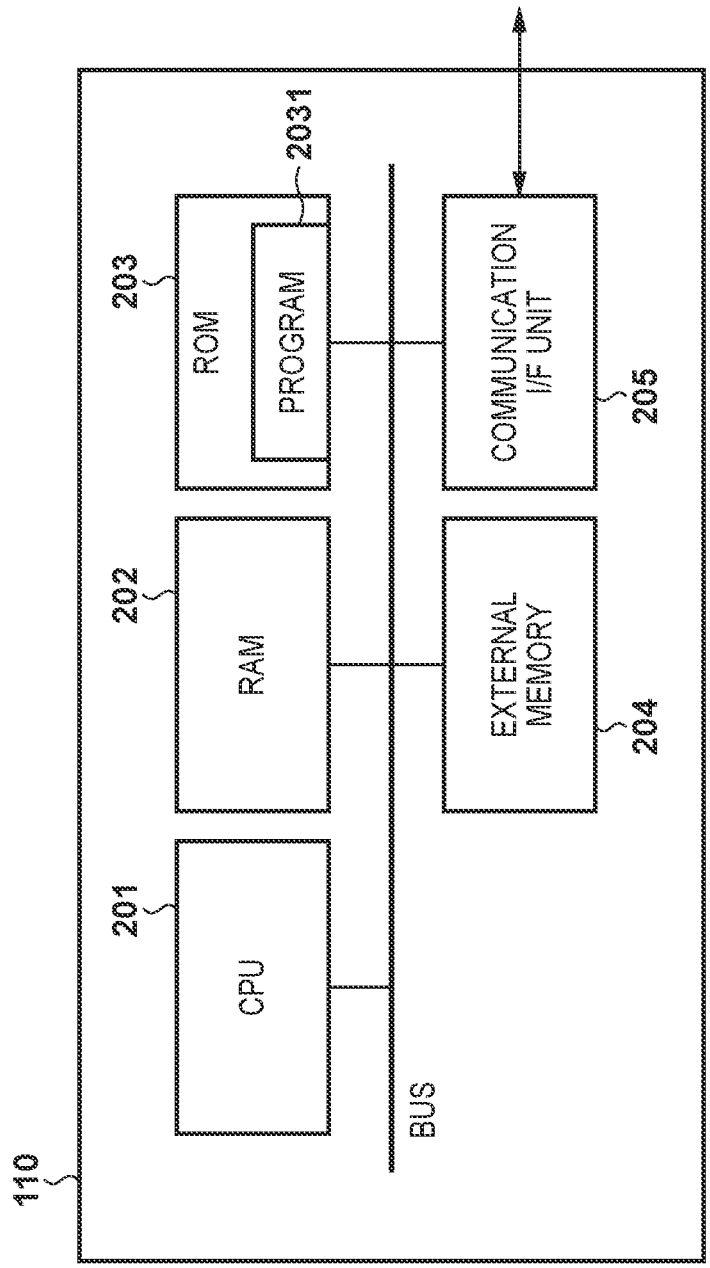
FIG. 2A is a block diagram showing an example of the hardware arrangement of a control apparatus.

Embodiments of the present invention will be described below with reference to the accompanying drawings.

First Embodiment

<1. Schematic Arrangement of Radiation Imaging System>

FIG. 1 is a schematic view showing an example of the schematic arrangement of a radiation imaging system 100 according to an embodiment (first embodiment) of the present invention. The radiation imaging system 100 includes a control apparatus 110, radiation generating units 114A, 114B, and 114C, radiation detectors 115A, 115B, and 115C, a RIS 130, a PACS 140, and a HIS 150. MS is the abbreviation of Radiology Information Systems. PACS is the abbreviation of Picture Archiving and Communication Systems (image server). HIS is the abbreviation of Hospital Information Systems. The radiation generating units 114A, 114B, and 114C will be collectively referred to as radiation generating units 114, and the radiation detectors 115A, 115B, and 115C will be collectively referred to as radiation detectors 115 hereinafter.

The control apparatus (imaging control apparatus) 110 is connected to a display unit 112, an operation unit 113, the radiation generating units 114A, 114B, and 114C, and the plurality of radiation detectors 115A and 115B via wired communication, and controls the operation by communicating with the devices. The wired communication can be executed via a LAN (Local Area Network) such as Ethernet®, but communication may be performed by another communication method. The radiation detector 115C is connected to the control apparatus 110 via wireless communication, and the control apparatus 110 controls the operation of the radiation detector 115C via the wireless communication. Although the wireless communication between the radiation detector 115C and the control apparatus 110 is executed via a wireless LAN, it may be executed by another wireless communication method such as Bluetooth® or the like. The control apparatus 110 is also connected to the RIS 130, the PACS 140, and the HIS 150 via a network 120 and can exchange radiation images, pieces of patient information, and the like.

The display unit 112 displays imaging examination information, captured radiation images, and various kinds of information. The operation unit 113 accepts input information from an operator. In this embodiment, the display unit 112 is a monitor (for example, a liquid crystal display or the like) and the operation unit 113 is formed from a keyboard, a pointing device (for example, a mouse or the like), and a touch panel.

The radiation generating units (radiation generating apparatuses) 114A, 114B, and 114C include radiation tubes configured to generate radiation and irradiate patients 1000A, 1000B, and 1000C who are the objects, respectively, with the radiation. The patient 1000A is in a standing position, the patient 1000B is in a supine position, and the patient 1000C is in a position other than these positions, and the radiation generating units 114A, 114B, and 114C and the radiation detectors 115A, 115B, and 115C are arranged at positions suitable for imaging. Note that in this embodiment, the radiation generating units 114A, 114B, and 114C are installed in their respective rooms for performing radiation imaging as shown in FIG. 1, and this embodiment will describe an example in which the range of a location to be irradiated with radiation by each radiation generating unit 114 is limited to a predetermined range. However, a portable radiation-generating unit can be used as each radiation generating unit.

The plurality of radiation detectors (radiation imaging apparatuses) 115A, 115B, and 115C generate images based on the radiation emitted from the radiation generating units 114A, 114B, and 114C, respectively. The control apparatus 110 performs image processing on radiation image data detected and obtained by each of the radiation detectors 115A, 115B, and 115C, and displays the obtained radiation image data as a radiation image on the display unit 112. The radiation detectors 115A and 115B are installed in a room and on a desk in accordance with the ranges of the locations to be irradiated with radiation by the radiation generating units 114A and 114B. On the other hand, since the radiation detector 115C is a portable radiation detecting apparatus, it is connected to the control apparatus 110 via wireless communication as described above. This embodiment will describe an example in which a plurality of devices which are of the same type are present to serve as the radiation detector 115C, and one of these devices will be used to detect the radiation emitted from the radiation generating unit 114C.

Note that although the radiation imaging system 100 according to this embodiment is described as an arrangement which includes the RIS 130, the PACS 140, and the HIS 150, it may have an arrangement which does not include at least some of these components.

In addition, although FIG. 1 shows an example in which the radiation generating units 114A, 114B, and 114C and the radiation detectors 115A, 115B, and 115C are present as the radiation generating units and the radiation detectors, respectively, the combinations of the radiation generating units and the radiation detectors are not limited to these. For example, the radiation imaging system 100 may include even more combinations of the radiation generating units and the radiation detectors.

<2. Arrangement of Control Apparatus>

An example of the arrangement of the control apparatus 110 according to the embodiment will be described next. First, FIG. 2A is a schematic block diagram showing an example of the hardware arrangement of the control apparatus 110. The control apparatus 110 includes a CPU 201, a RAM 202, a ROM 203, an external memory 204, and a communication I/F unit 205, and these components are connected to each other via a bus.

The CPU (Central Processing Unit) 201 is a unit configured to control the overall operation of the control apparatus 110, and controls the components (the RAM 202 to the communication I/F unit 205) shown in FIG. 2A via the bus.

The RAM (random access memory) 202 functions as the main memory of the CPU 201, the work area, and the like. When executing processing, the CPU 201 loads a required computer program 2031 and basic data from the ROM 203 to the RAM 202 and executes the computer program 2031 to implement various kinds of function operations. The ROM (read-only memory) 203 stores the computer program 2031 and the basic data required for the CPU 201 to execute processing. Note that the computer program 2031 may be stored in the external memory 204.

The external memory 204 is a large capacity storage device and is implemented by, for example, a hard disk device, an IC memory, or the like. The external memory 204 stores, for example, various kinds of data and various kinds of information required when the CPU 201 is to execute processing using the computer program 2031 or the like. In addition, the external memory 204 stores, for example, various kinds of data and various kinds of information obtained by the CPU 201 by executing processing using the computer program 2031 or the like.

The communication I/F (interface) unit 205 is a unit in charge of communication with the outside. The bus communicably connects the CPU 201, the RAM 202, the ROM 203, the external memory 204, and the communication OF unit 205 to each other.

Although the control apparatus 110 according to this embodiment will be provided as a dedicated embedded device, it may be implemented by a general-purpose information processing apparatus such as a PC (personal computer), a tablet terminal, or the like.

Figure 2B:
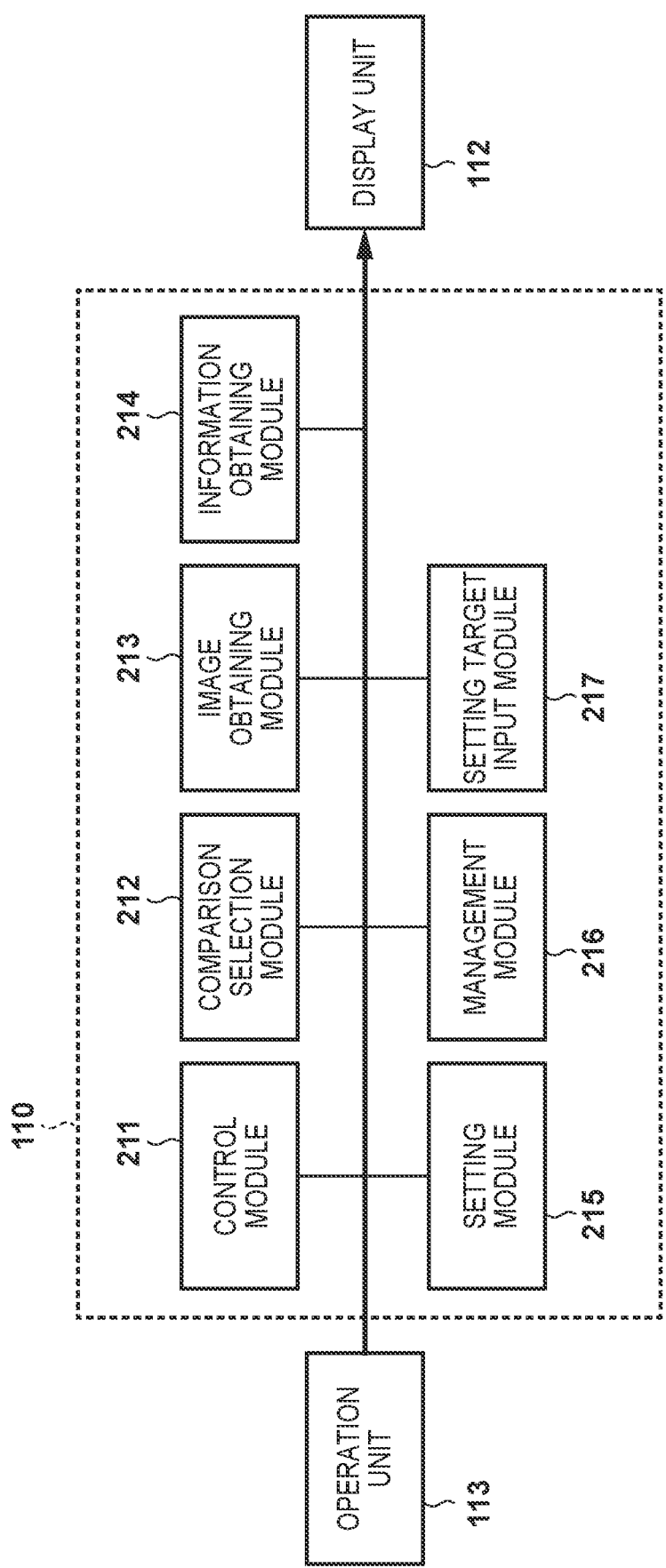
FIG. 2B is a block diagram showing an example of the software arrangement of the control apparatus.

FIG. 2B is a functional block diagram showing the software arrangement of the control apparatus 110 according to this embodiment. The control apparatus 110 includes a control module 211, a comparison selection module 212, an image obtaining module 213, an information obtaining module 214, a setting module 215, a management module 216, and a setting target input module 217. Each function is implemented by the CPU 201 loading the computer program 2031 stored in the ROM 203 to the RAM 202 and executing the loaded computer program.

The control module 211 performs presence/absence determination, creates, and edits the various kinds of setting information set in the radiation imaging system 100. The comparison selection module 212 selects the radiation detectors 115A and 115B based on the information obtained by the information obtaining module 214. The image obtaining module 213 obtains a radiation image from each radiation detector selected by the comparison selection module 212. The information obtaining module (radiation detector information obtaining module) 214 obtains radiation detector information from the each of the radiation detectors 115A and the 115B that has performed radiation imaging or obtains information when radiation irradiation is performed from each of the radiation generating units 114A and 114B.

The setting module (imaging target setting module) 215 sets, to each radiation detector registered in the radiation imaging system 100, whether it is a radiation detector to be used for imaging. The management module (installation state management module) 216 manages the installation state such as whether a radiation detector is installed in a standing-position platform, in a supine-position table, or the like. The setting target input module 217 accepts an operation made by the user to set whether a radiation detector is the radiation detector is to be used.

Note that the functional blocks described above are merely examples, and the control apparatus 110 may have an arrangement which does not include some of the functional blocks described above or may have an arrangement which includes further functional blocks.

<3. Sequence of Radiation Imaging>

Figure 3:
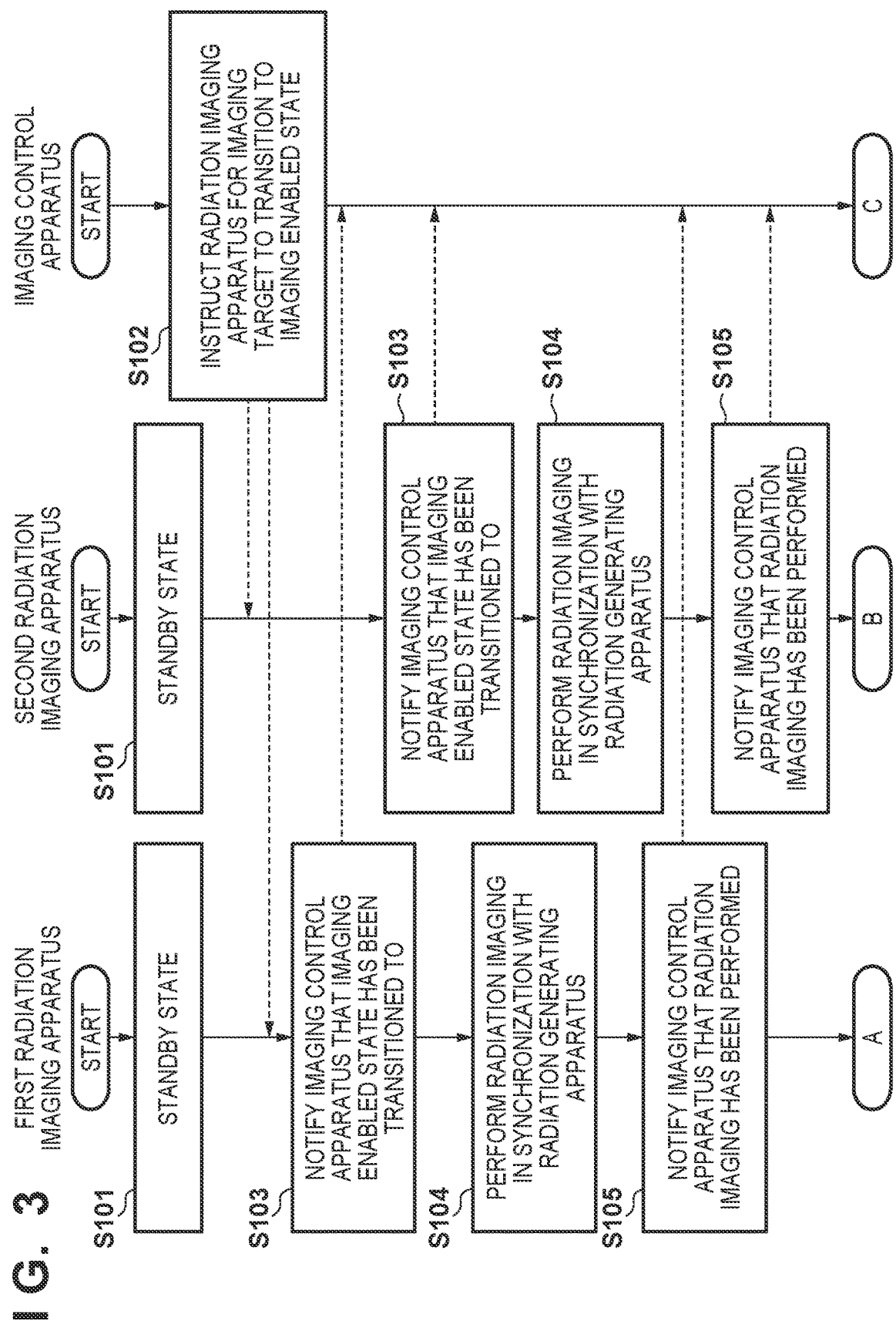
FIG. 3 is a flowchart showing a radiation imaging operation.

FIG. 3 is a flowchart showing an example of operations performed by the imaging control apparatus (control apparatus) 110 and the first and second radiation imaging apparatuses (the radiation detectors) 115 from the preparation for a radiation imaging operation to the execution of the radiation imaging operation. Note that the operation of the control apparatus 110 is implemented by the CPU 201 executing a predetermined computer program. The operation of the first radiation imaging apparatus (for example, 115A) and the operation of the second radiation imaging apparatus (for example, 115B) are implemented by a CPU (not shown) of each radiation imaging apparatus executing a predetermined computer program stored in a memory (not shown). Also, although the following description will exemplify a case in which the radiation detectors 115A and 115B are present as the plurality of radiation imaging apparatuses, another radiation detector (for example, 115C) may also be present.

In step S101, the first radiation imaging apparatus 115A and the second radiation imaging apparatus 115B are set to a standby state. In the standby state, communication is established between the radiation imaging apparatuses 115 and the control apparatus 110. In step S102, the control apparatus 110 transmits, to all of the radiation imaging apparatuses 115 that can be used, a transition instruction to cause each radiation imaging apparatus to transition to an imaging enabled state. In this embodiment, the first radiation imaging apparatus 115A and the second radiation imaging apparatus 115B are the radiation imaging apparatuses that can be used.

In step S103, the first radiation imaging apparatus 115A and the second radiation imaging apparatus 115B each transition to an imaging enabled state in response to the transition instruction from the control apparatus 110 and notify the control apparatus 110 of the completion of the transition to the imaging enabled state. Next, in step S104, the first radiation imaging apparatus 115A and the second radiation imaging apparatus 115B execute a radiation imaging operation in synchronization with the corresponding radiation generating apparatuses (radiation generating units) 114. In step S105, the first radiation imaging apparatus 115A and the second radiation imaging apparatus 115B each notify the control apparatus 110 of the execution of the radiation imaging operation.

Figure 4:
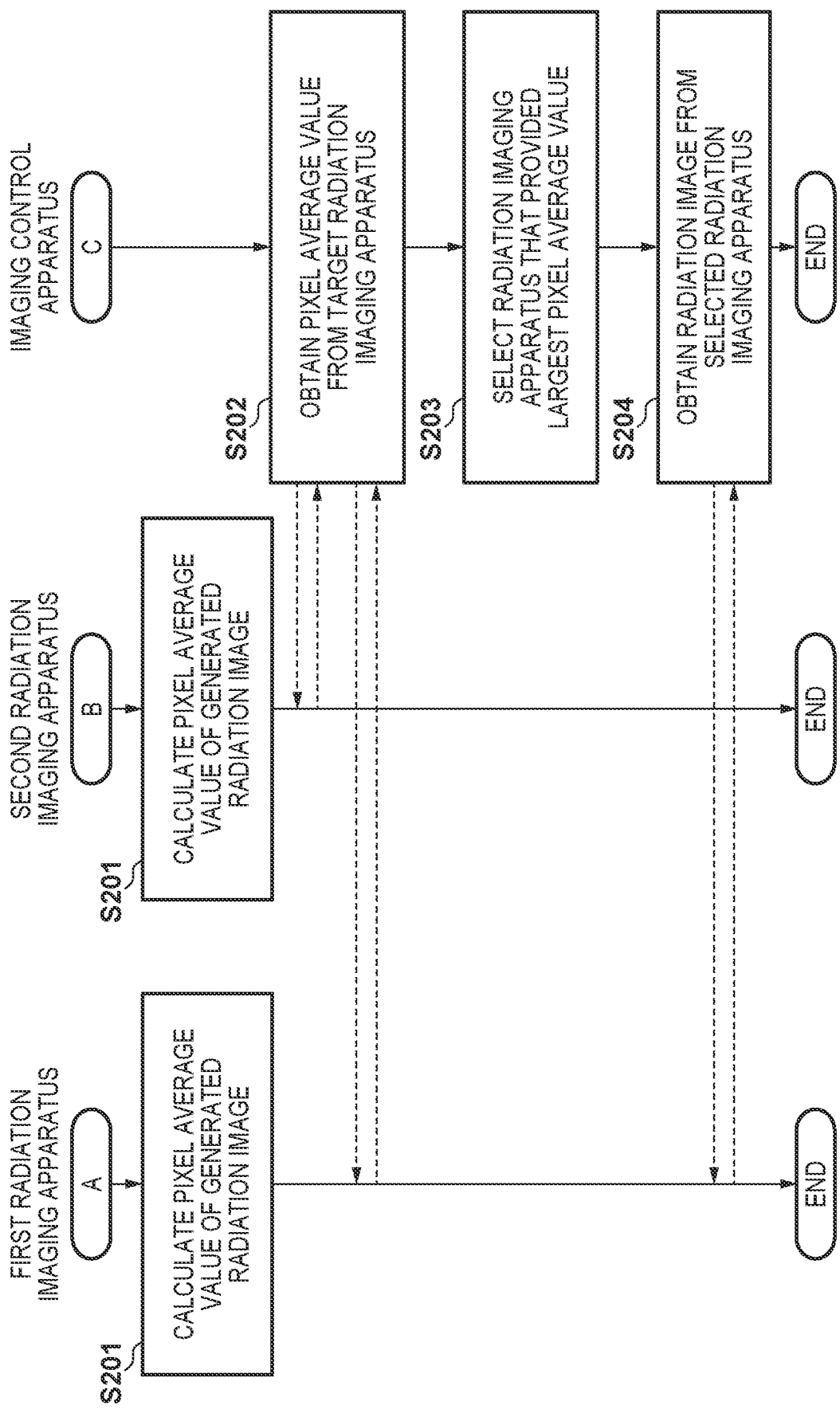
FIG. 4 is a flowchart showing a radiation image obtaining operation.

FIG. 4 is a flowchart showing an example of operations performed until the control apparatus 110 obtains a radiation image after a radiation imaging operation has been executed by each of the first radiation imaging apparatus 115A and the second radiation imaging apparatus 115B.

In step S201, each of the first radiation imaging apparatus 115A and the second radiation imaging apparatus 115B calculates statistic information of pixel values from the generated radiation image. Each of the radiation imaging apparatuses 115 transmits the calculated statistic information to the control apparatus 110 as imaging information. Assume here that the average value (to be referred to as pixel average value hereinafter) of the pixel values as an example of statistic information. The statistic information is not limited to this as a manner of course, and for example, the maximum value, the median, or the variance value or the like may be used. Alternatively, the statistic information may be the maximum value of the difference between the pixel values of adjacent pixels, the width between the maximum value and the minimum value of the pixel values, or the like. There may be two or more pieces of the statistic information to be calculated. Note that each pixel value may be a luminance value or a density value. Furthermore, the imaging information may be an image (for example, a thinned-out image, a reduced image, or the like) having a data size smaller than a captured image that has been generated based on the captured image. In S202, the control apparatus 110 (the information obtaining module 214) obtains the pixel average value calculated in step S201 from each of the first radiation imaging apparatus 115A and the second radiation imaging apparatus 115B.

In step S203, the control apparatus 110 (the comparison selection module 212) compares the pixel average values obtained in step S202 and selects the radiation imaging apparatus that provided the largest pixel average value. Note that although an arrangement in which the radiation imaging apparatus that provided the largest pixel average value is selected has been shown above, the present invention is not limited to this. For example, it may be set so that the radiation imaging apparatus that provided statistic information closest to a preset threshold will be selected. It also may be set so that the radiation imaging apparatus will be selected by comparing a plurality of pieces of statistic information. In addition, in a case in which a single radiation imaging apparatus cannot be selected because the comparison results are identical, it may be set so that the radiation imaging apparatus that transmitted the radiation imaging execution notification first will be selected. In step S204, the control apparatus 110 (the image obtaining module 213) obtains a radiation image from the radiation imaging apparatus (assume that the first radiation imaging apparatus 115A has been selected in this case) selected in step S203. That is, the control apparatus 110 makes an image request to the first radiation imaging apparatus 115A, and the first radiation imaging apparatus 115A transmits the radiation image to the control apparatus 110 in response to the image request from the control apparatus 110.

As described above, in a system in which radiation imaging is executed by setting a plurality of radiation imaging apparatuses in an imaging enabled state, the control apparatus 110 will select a radiation imaging apparatus for obtaining a radiation image based on imaging information (for example, pixel average value) having a data size smaller than the radiation image. Since the control apparatus 110 will obtain the radiation image from the selected radiation imaging apparatus, the radiation imaging cycle can be shorter than in an arrangement in which radiation images are obtained from all of the radiation imaging apparatuses. Hence, it is possible to implement a radiation imaging system that can perform radiation imaging at a quick cycle while reducing the possibility of unnecessary radiation exposure due to re-imaging.

<4. Example of Imaging Target Setting Screen>

Figure 5:
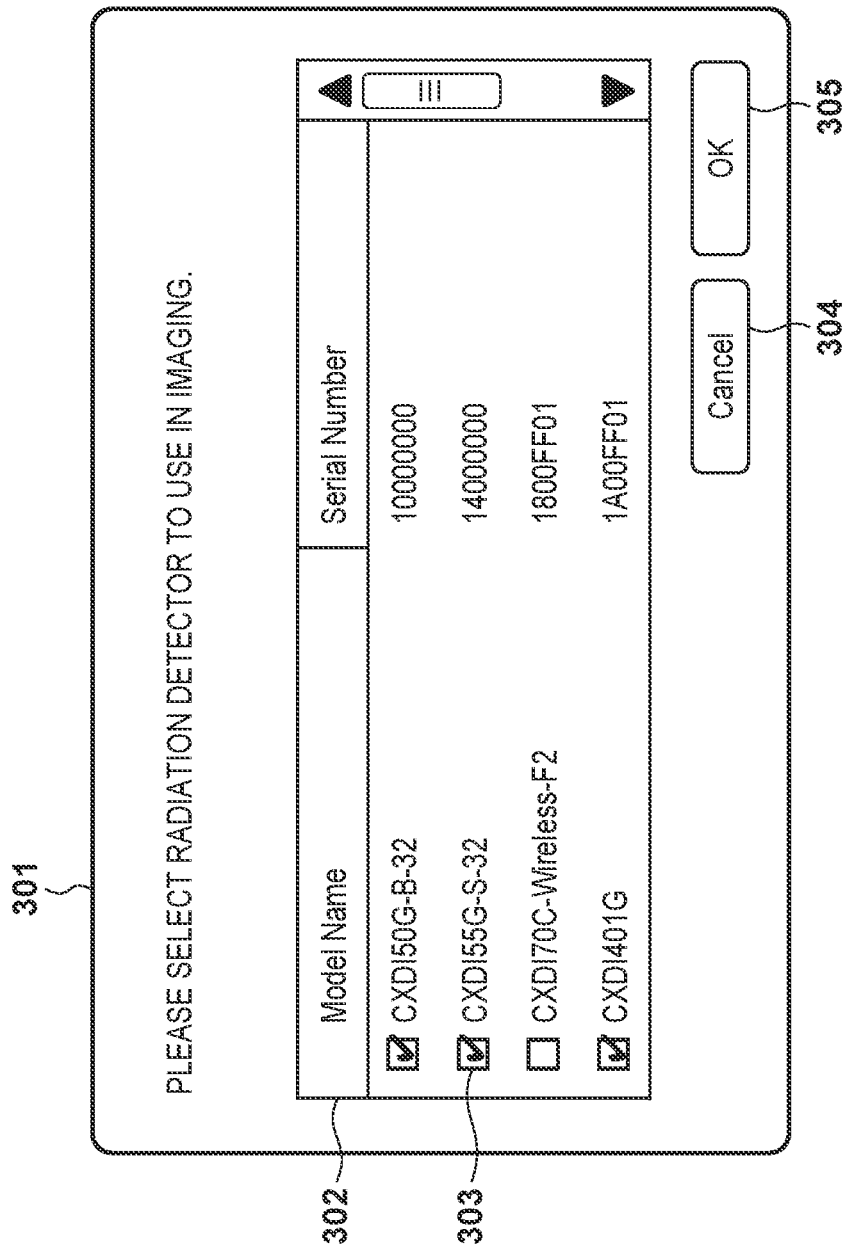
FIG. 5 is a view showing an example of a setting screen of a radiation detector to be used for imaging.

FIG. 5 is a view showing an example of an imaging target setting screen 301 to be displayed on the display unit 112 according to this embodiment. The imaging target setting screen 301 includes a radiation detector display region 302, imaging target enabling checkboxes 303, a setting complete button 304, and a setting cancel button 305.

A list of radiation detectors registered in the radiation imaging system 100 is displayed in the radiation detector display region 302. Each imaging target enabling checkbox 303 is a checkbox for enabling a radiation detector designated by the operator as an imaging target. The setting cancel button 304 is a button for the operator to instruct the cancellation of the imaging target setting. The setting complete button 305 is a button for the operator to instruct the confirmation of the setting contents of the imaging target.

<5. Example of Processing to Set Imaging Target Radiation Detector>

Figure 6:
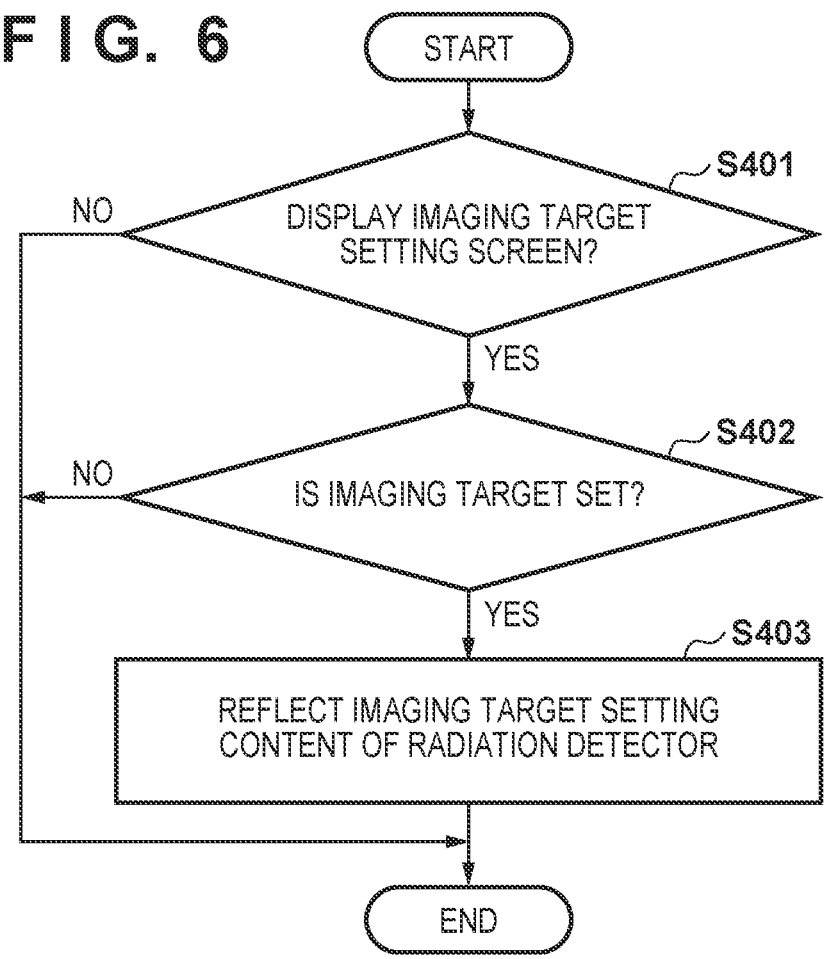
FIG. 6 is a flowchart showing a processing procedure to set an imaging target radiation detector.

FIG. 6 is a flowchart showing a processing procedure to set an imaging target radiation detector in the radiation imaging system 100 according to this embodiment. Each step of FIG. 6 is executed by the CPU 201 of the control apparatus 110 controlling the radiation imaging system 100 based on the computer program 2031.

First, in step S401, the control module 211 determines whether the imaging target setting screen 301 shown in FIG. 5 has been displayed on the display unit 112. If the imaging target setting screen has been displayed (YES in step S401), the process advances to step S402. On the other hand, if the imaging target setting screen has not been displayed (NO in step S401), the processing ends.

In step S402, the setting target input module 217 determines whether the imaging target setting of each radiation detector has been input by the operator. If the imaging target setting has been input (YES in step S402), the process advances to step S403. On the other hand, if the imaging target setting has not be input (NO in step S402), the processing ends.

In step S403, the imaging target setting contents of each radiation detector set in step S402 are reflected by the setting module 215. That is, the setting module obtains imaging information such as the statistic information of the captured image from each radiation detector set as an imaging target by the operator in step S402 and does not obtain imaging information from other radiation detectors.

The processes of the flowchart of FIG. 6 are completed as described above. After this processing, radiation is generated from one of the radiation generating units 114A, 114B, and 114C in accordance with the operation made on the operation unit 113 by the operator. Subsequently, the imaging information such as the statistic information of the captured image from each radiation detector set in step S403 is obtained, a radiation detector is selected from the plurality of radiation detectors based on the pieces of imaging information, and an image obtainment operation of obtaining an image from the selected radiation detector is performed.

As described above, the control apparatus 110 according to this embodiment obtains imaging information from each of the plurality of the radiation detectors 115, selects a radiation detector from the plurality of radiation detectors based on the obtained pieces of imaging information, and obtains an image from the selected radiation detector. Assume here that the control apparatus 110 sets each radiation detector for imaging information obtainment and obtains the imaging information from only each set radiation detector. More specifically, display control is performed to cause the display unit 112 to display a screen that allows each radiation detector to be used for imaging to be selected from the plurality of radiation detectors, and each radiation detector selected by the operator via this screen is set as the radiation detector for imaging information obtainment. By setting the radiation detector for imaging information obtainment in accordance with the instruction from the operator in this manner, it becomes possible for the operator to arbitrarily set an imaging target radiation detector on the imaging target setting screen 301. As a result, it becomes possible to narrow down the radiation detectors for imaging information obtainment used to select a radiation detector for captured image obtainment without having to set all of the radiation detectors registered in the radiation imaging system 100 in an imaging enabled state. Hence, a captured image can be obtained from a radiation imaging apparatus that has actually performed imaging. Therefore, it becomes possible to suppress a reduction in imaging efficiency due to a state in which radiation detectors necessary for the detection of radiation irradiation are not set to a detectable state and reduce the risk of unnecessary exposure on the human body.

In addition, the radiation imaging system according to this embodiment includes a plurality of radiation detectors (imaging apparatuses) configured to generate images based on radiation emitted from the radiation generating units (radiation generating apparatuses) and a control apparatus configured to communicate with a plurality of radiation generating units. Assume here that at least two radiation detectors are selected from the plurality of radiation detectors and that pieces of imaging information of images generated by the at least two radiation detectors that have been selected are obtained. Among the plurality of radiation detectors, at least two radiation detectors are selected here by excluding at least one radiation detector. Subsequently, an image obtainment operation is performed by selecting one radiation detector from the at least two radiation detectors based on the pieces of the obtained imaging information and obtaining an image from the selected radiation detector. In this manner, in this embodiment, instead of obtaining the pieces of imaging information from all of the radiation detectors, the pieces of imaging information are obtained after selecting the radiation detectors for imaging information obtainment, and subsequently the radiation detector for image obtainment is selected. Therefore, even in a case in which some of the radiation detectors are disconnected from communication, a captured image can be obtained from the radiation detector that has performed the imaging.

Second Embodiment

The first embodiment described an example in which the operator sets an imaging target radiation detector on the imaging target setting screen 301 in accordance with the state. In contrast, the second embodiment will describe an example in which a radiation imaging system 100 will automatically set an imaging target based on the installation state of each radiation detector. Note that the arrangements of the radiation imaging system, a control apparatus, and the like according to this embodiment are the same as those of the first embodiment, thus a detailed description will be omitted.

In general, if a radiation generating unit which is to perform radiation irradiation has been already specified, a radiation detector for detecting the radiation emitted from this radiation generating unit is limited. For example, in the example shown in FIG. 1, if radiation irradiation is to be performed from a radiation generating unit 114A, only a radiation detector 115A can detect the emitted radiation, and no other option is possible. Similarly, if radiation irradiation is to be performed from a radiation generating unit 114B, only a radiation detector 115B can detect the emitted radiation.

On the other hand, if it is assumed that a radiation detector 115C is portable and performs wireless communication with a control apparatus 110 in the same manner as above, a plurality of devices of the same type can be present as this kind of a portable radiation detector. Hence, in a case in which radiation irradiation is to be performed by a radiation generating unit 114C, it will be not be immediately clear which radiation detector will detect the radiation if only the radiation generating unit is specified. That said, however, in a case in which radiation irradiation is to be performed by the radiation generating unit 114C, the radiation detectors 115A and 115B will not be used as a matter of course.

Therefore, in this embodiment, the radiation detector for imaging information obtainment will be set based on the installation state of the radiation detector or the radiation generating unit. That is, it is set so imaging information is obtained from only a corresponding radiation detector in accordance with the setting of each radiation generating unit 114 to be used and imaging information will not be obtained from other radiation detectors. More specifically, when the radiation detector to be used is apparent, such as in cases in which an imaging examination is to be performed in a standing position or a supine position, any radiation detector other than the corresponding radiation detector will be excluded as an imaging target and will be automatically excluded as a radiation detector for imaging information obtainment. That is, at least one radiation detector which does not correspond to the radiation generating unit to be used is excluded from the radiation detectors for imaging information obtainment. Hence, according to this embodiment, it becomes possible to reduce the time required until the transition to the imaging enabled state. In addition, the improvement of the imaging workflow efficiency can be expected since it saves the operator from having to manually set the radiation detector to be excluded as an imaging target.

Figure 7:
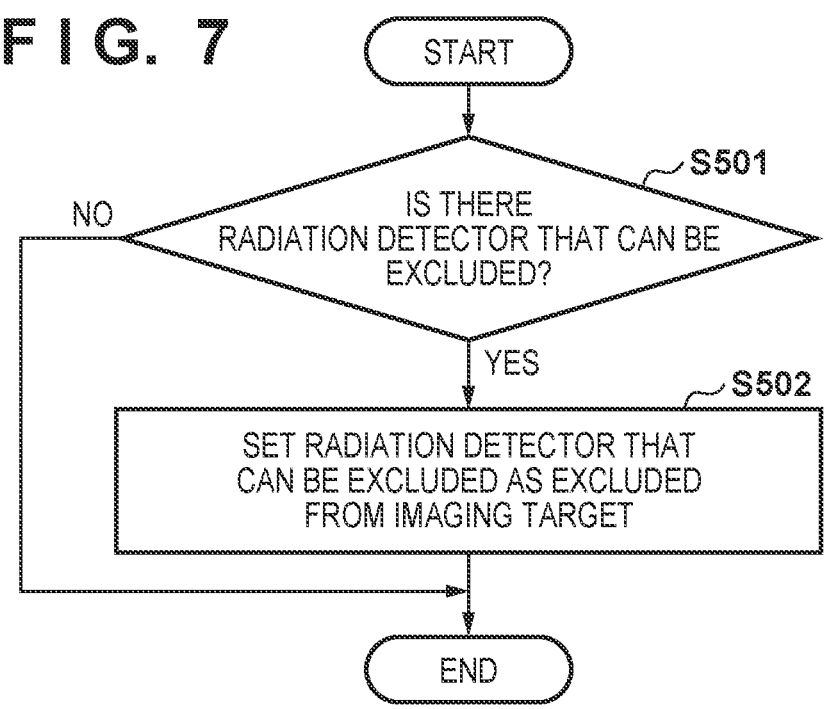
FIG. 7 is a flowchart showing a processing procedure to exclude a radiation detector from imaging targets based on an installation state.

FIG. 7 is a flowchart showing a processing procedure in which the control apparatus 110 according to the second embodiment automatically excludes a radiation detector from imaging targets when there is a radiation detector whose installation state can be limited. Each step of FIG. 7 is executed by a CPU 201 of the control apparatus 110 controlling the radiation imaging system 100 based on a computer program 2031.

First, in step S501, at the start of the examination, a management module 216 determines whether there is a radiation detector that can be excluded from radiation detectors to be used for imaging based on the installation states of the radiation detectors and the radiation generating unit 114 to be used registered in the radiation imaging system 100. The determination as to whether a radiation detector can be excluded from the radiation detectors to be used can be performed here, for example, based on the device installation state which includes connection information of a platform related to the radiation generating unit 114 and the like.

For example, in the example shown in FIG. 1, in case in which the radiation generating unit 114A is to be used to perform radiation irradiation, since only the radiation detector 115A will detect the radiation, the other radiation detectors 115B and 115C can be set as the radiation detectors that can be excluded. In the same manner, in a case in which the radiation generating unit 114B is to be used to perform radiation irradiation, since only the radiation detector 115B will detect the radiation, the other radiation detectors 115A and 115C can be set as the radiation detectors that can be excluded.

In a case in which the radiation generating unit 114C is to be used to perform radiation irradiation, since the radiation detector 115C will detect the radiation, there are a plurality of radiation detectors that can serve as the radiation detector 115C. Hence, it is impossible to immediately specify which of the radiation detectors is to be used based on only a piece of information indicating the use of the radiation generating unit 114C. However, it is evident from the device installation state of the radiation imaging system 100 shown in FIG. 1 that at least the radiation detectors 115A and 115B will not be used in the case in which the radiation generating unit 114C is to be used. Therefore, in a case in which the radiation generating unit 114C is to be used to perform radiation irradiation, the radiation detectors 115A and 115B can be set as radiation detectors that can be excluded.

In this manner, in step S501, the presence/absence of each radiation detector 115 that can be excluded from use-target detectors is determined based on the installation state of the radiation generating units 114 and the radiation detectors 115. This kind of determination can be made by presetting and using, for example, information that indicates the correspondence relationship between each radiation generating unit 114 and the radiation detector 115 which is to be used when this radiation generating unit is used. More specifically, the corresponding radiation detector 115 can be specified in accordance with the selection of the radiation generating unit 114, and each radiation detector other than the specified radiation detector can be determined to be the radiation detector 115 that can be excluded.

Note that the information indicating the device installation state is not limited to information indicating the correspondence relationship between devices in this manner. For example, the position information of the radiation generating units 114 and the radiation detectors 115, wiring information of the devices, or the like may be used.

Alternatively, information indicating an imaging execution state can be used as the information indicating the device installation state. Such imaging execution information includes, for example, the posture of a measurement subject (the patient), the use state of the radiation detector 115 (whether the radiation detector is installed on a platform, whether the radiation detector is to be laid flat and used, and the like), or the like. If information based on the posture of the patient is to be used, the correspondence relationship between the radiation detector 115 to be used and imaging execution states such as the standing position, the supine position, and the like is stored, and each radiation detector other than the corresponding radiation detector that can be determined to be a radiation detector which can be excluded in accordance with the selection of the imaging execution state. If information based on the installation state of the radiation detector 115 is to be used, the correspondence relationship between the radiation detector 115 to be used and the use states of the radiation detector such as, for example, "laid flat", "installed on a platform", and the like can be stored. In this case, each radiation detector other than the corresponding radiation detector that can be determined to be a radiation detector can be excluded in accordance with the selection of the use state. In this manner, in a case in which a radiation generating unit for imaging a human body in a specific posture or a specific part of the human body is to be used, predetermined radiation detectors can be excluded as the radiation detector for imaging information obtainment.

If there is a radiation detector that can be excluded based on the installation state by performing such processing as described above (YES in step S501), the process advances to step S502. On the other hand, if a radiation detector that can be excluded is not present (NO in step S501), the processing ends.

In step S502, a setting module 215 sets, as an imaging target excluded radiation detector, each radiation detector that can be excluded from the radiation detectors to be used for imaging based on the installation state. The setting module 215 excludes each radiation detector (radiation imaging apparatus) whose communication is disconnected from the radiation detectors (radiation imaging apparatuses) for obtaining imaging information. That is, the imaging information is not obtained from each radiation detector determined to be an exclusion target in step S501, and imaging information is obtained from radiation detectors obtained from other radiation detectors.

The processes of the flowchart of FIG. 7 are completed as described above. After this processing, radiation generation is performed from one of the radiation generating units 114A, 114B, and 114C in accordance with the operation made on the operation unit 113 by the operator, and the imaging information is obtained from each radiation detector 115 other than the radiation detectors that were excluded in step S502. Subsequently, the radiation detector for captured image obtainment is selected based on the imaging information, and the captured image is obtained from the selected radiation detector.

As described above, according to the second embodiment, a radiation detector can be automatically excluded from imaging target radiation detectors based on the installation state. As a result, in the case of an examination in which imaging is performed by setting the radiation detector in a laid flat state, it is possible to expect a reduction in the time required until the transition to the imaging enabled state by automatically excluding, from the imaging target, each radiation detector which is installed in a platform or the like. In addition, further improvement in the imaging workflow efficiency can be expected since it saves the operator from having to manually set the radiation detector to be excluded as an imaging target.

Third Embodiment

The second embodiment described an example in which an imaging target is automatically set based on the installation state of the radiation detector. In contrast, the third embodiment will describe an example in which the imaging target is automatically set based on imaging examination information. Note that the arrangements of the radiation imaging system, the control apparatus, and the like are the same as those of the first embodiment, and thus a description will be omitted.

The imaging examination information is examination information indicating the contents of the examination performed by radiation imaging. The imaging examination information is manually input to a radiation imaging system 100 directly by an operation input made by an operator or automatically input to the radiation imaging system 100 from an external apparatus such as a HIS or a RIS via a network. Information including different combinations of the imaging part, imaging posture, the imaging direction, and the like of an object is included in this imaging examination information. Hence, when imaging operations are to be performed in a case in which the imaging posture is the standing position and the supine position, it is difficult to make a mistake in radiation detector selection since it is evident that radiation detectors installed in a platform, a table, and the like will be used.

Thus, in this embodiment, this kind of imaging examination information is obtained, and each radiation detector for imaging information obtainment is set based on its contents. As a result, a radiation detector which clearly will not be used is excluded from use targets. According to this embodiment, imaging information can be obtained from only a necessary radiation detector based on the contents of the imaging examination information without obtaining imaging information from an unnecessary radiation detector. This can suppress the reduction in imaging efficiency due to a state in which radiation detectors necessary for the detection of radiation irradiation are not set to a detectable state and reduce the risk of unnecessary exposure on the human body. Therefore, the time until the transition to the imaging enabled state is reduced.

Figure 8:
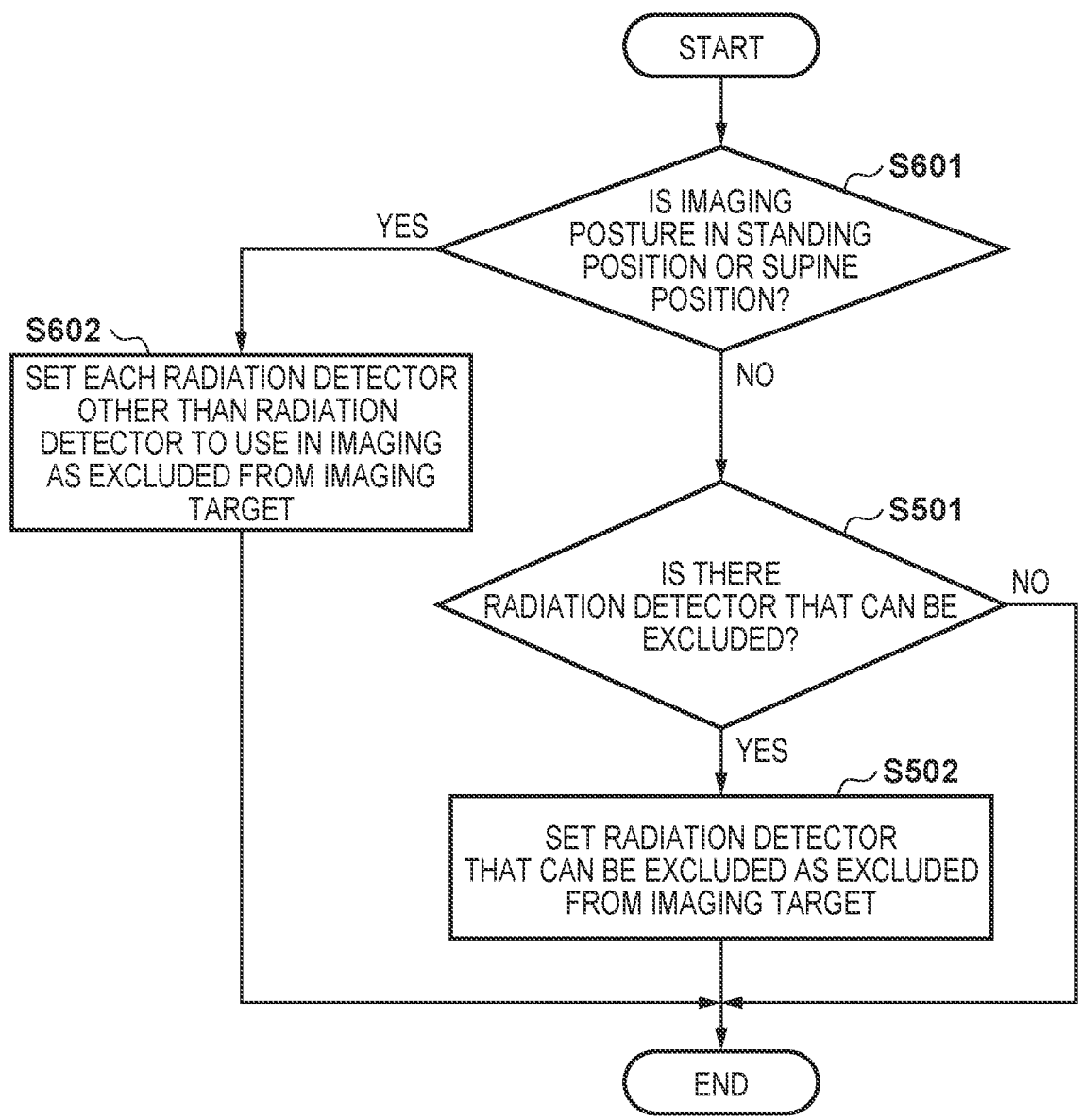
FIG. 8 is a flowchart showing a processing procedure to set an imaging target based on imaging examination information.

FIG. 8 is a flowchart showing a processing procedure in which a control apparatus 110 according to the third embodiment automatically sets an imaging target based on the imaging examination information. Same reference numerals denote processes which are the same as those of FIG. 7, and a description thereof will be omitted. Each step of FIG. 8 is executed by a CPU 201 of the control apparatus 110 controlling the radiation imaging system 100 based on a computer program 2031.

First, in step S601, at the start of an examination, a control module 211 determines whether it is an examination in which imaging is to be performed by setting the imaging posture in a standing position or a supine position. This determination is performed based on the contents of the imaging examination information. If it is determined to be an examination in which imaging is to be performed in the standing position or the supine position (YES in step S601), the process advances to step S602. On the other hand, if it is determined not to be an examination in which imaging is to be performed in the standing position or the supine position (NO in step S601), the process advances to step S501.

The processing contents for step S501 and the subsequent steps are the same as those in the second embodiment other than the process in which the contents of the imaging examination information are referred to. That is, based on the installation states of radiation generating units 114 and radiation detectors 115, each radiation detector 115 that can be excluded from an imaging information obtainment target is excluded from radiation detectors to be set in an imaging enabled state. In the example of the radiation imaging system 100 shown in FIG. 1, an imaging posture other than the standing position and the supine position is the imaging posture using a radiation detector 115C which is flatly laid. In this case, since the use of radiation detectors 115A and 115B will be determined to be unnecessary (YES in step S501), these radiation detectors will be excluded from use targets (step S502).

In step S602, a setting module 215 sets each radiation detector other than the radiation detector to be used for imaging to be excluded from imaging information obtainment targets. In the example shown in FIG. 1, imaging performed in the standing position is performed by using a radiation generating unit 114A and the radiation detector 115A, and imaging performed in the supine position is performed by using a radiation generating unit 114B and the radiation detector 115B. Hence, in the case of imaging in the standing position, the radiation detectors 115B and 115C, which are radiation detectors other than the radiation detector 115A, are excluded from the imaging information obtainment targets. In the case of imaging in the supine position, the radiation detectors 115A and 115C, which are radiation detectors other than the radiation detector 115B, are excluded from the imaging information obtainment targets. The processes of the flowchart of FIG. 8 are completed as described above.

As described above, according to the third embodiment, an imaging target can be automatically set based on the imaging examination information. As a result, by automatically excluding each radiation detector other than that to be used for imaging from imaging targets in an examination in which imaging is to be performed in an imaging posture such as the standing position or the supine position, it becomes possible to suppress a reduction in imaging efficiency and reduce the risk of unnecessary exposure on the human body. Therefore, the time until the transition to the imaging enabled state is reduced.

Fourth Embodiment

Figure 9:
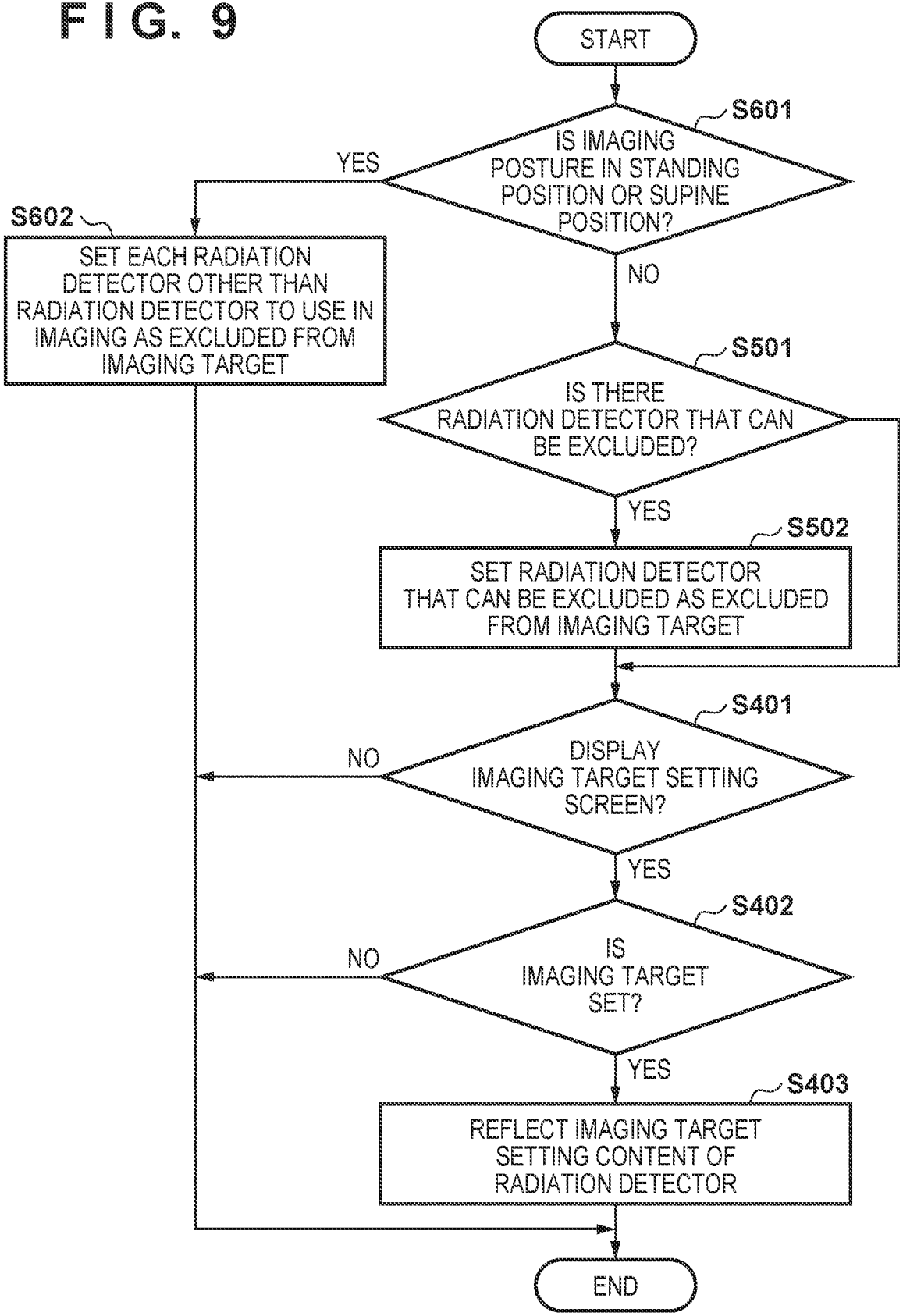
FIG. 9 is a flowchart showing an example of a processing procedure to set an imaging target of a radiation detector.

In the fourth embodiment, setting of an imaging target of a radiation detector may be performed by combining the imaging target setting methods implemented in the first embodiment to the third embodiment as shown in FIG. 9.

FIG. 9 is a flowchart showing a processing procedure in which a control apparatus 110 according to this embodiment sets an imaging target. The same reference numerals are used for processes which are the same as those in FIGS. 6 to 8, and a detailed description thereof will be omitted. Each step shown in FIG. 9 is executed by a CPU 201 of the control apparatus 110 controlling a radiation imaging system 100 based on a computer program 2031. The processes of steps S601, S602, S501, and S502 are the same as those of FIG. 8. In this embodiment, the process will advance to step S401 after the process of step S502 as a matter of course. The processes of steps S401 to S403 are the same as those of FIG. 6.

In this embodiment, when imaging examination information is obtained, each radiation detector for imaging information obtainment is excluded based on the contents of the imaging examination information in steps S601 and S602. Next, in steps S501 and S502, each radiation detector without any possibility of use is excluded from the radiation detectors for imaging information obtainment based on the installation state of a radiation detector or a radiation generating unit. In this manner, after the radiation detectors for imaging information obtainment are narrowed down, the radiation detectors for imaging information obtainment are set in accordance with an instruction from the operator in steps S401 to S403. In this embodiment, after the radiation detectors for imaging information obtainment have been automatically narrowed down by the processes of steps S601, S602, S501, and S502, a user instruction is input in the processes of steps S401 to S403. Hence, the setting of the radiation detectors for imaging information obtainment can be performed easily and reliably.

As described above, according to the embodiments of the present invention, a radiation imaging system that suppresses a reduction in the imaging efficiency when there are a plurality of radiation detectors to be used for imaging can be provided. Therefore, radiation imaging can be performed efficiently even when not every radiation detector is set in the imaging enabled state.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

According to the present invention, a technique that allows radiation imaging to be performed efficiently even in a case in which not every radiation detector is set to an imaging enabled state can be provided.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiation imaging system comprising a plurality of imaging apparatuses which are arranged in one imaging room and are configured to generate images based on radiation emitted from radiation generating apparatuses configured to perform radiation irradiation and a control apparatus configured to communicate with the plurality of imaging apparatuses, wherein the control apparatus comprises:

one or more processors; and a memory including instructions stored thereon that, when executed by the one or more processors, cause the control apparatus to function as:
an obtainment unit configured to obtain imaging information from each of the plurality of imaging apparatuses;
a selection unit configured to select one imaging apparatus from the plurality of imaging apparatuses based on the imaging information obtained by the obtainment unit;
an image obtainment unit configured to obtain an image from the imaging apparatus selected by the selection unit; and
a setting unit configured to set, from the plurality of imaging apparatuses arranged in the one imaging room, an imaging apparatus from which imaging information is obtained by the obtainment unit.

2. The radiation imaging system according to claim 1, wherein the obtainment unit obtains the imaging information from the imaging apparatus set by the setting unit.

3. The radiation imaging system according to claim 1, wherein the setting unit sets the imaging apparatus from which the imaging information is obtained in accordance with an instruction from an operator.

4. The radiation imaging system according to claim 3, wherein the instructions, when executed by the one or more processors, further cause the control apparatus to function as:
a display control unit configured to cause a display apparatus to display a screen on which an imaging apparatus to be used for imaging can be selected from the plurality of imaging apparatuses, and
wherein the setting unit sets an imaging apparatus selected by the operator as the imaging apparatus from which the imaging information is obtained.

5. The radiation imaging system according to claim 1, wherein the setting unit sets the imaging apparatus from which the imaging information is obtained based on an installation state of the imaging apparatus or the radiation generating apparatus.

6. The radiation imaging system according to claim 5, wherein the setting unit excludes at least one imaging apparatus from the imaging apparatuses from which the imaging information is obtained.

7. The radiation imaging system according to claim 6, wherein in a case in which a radiation generating apparatus for imaging a human body in a specific posture or a specific part of the human body is to be used, the setting unit excludes a predetermined imaging apparatus from the imaging apparatuses from which the imaging information is obtained.

8. The radiation imaging system according to claim 5, wherein the setting unit excludes an imaging apparatus whose communication has been disconnected from the imaging apparatuses from which the imaging information is obtained.

9. The radiation imaging system according to claim 1, wherein the instructions, when executed by the one or more processors, further cause the control apparatus to function as:
an information obtainment unit configured to obtain examination information indicating contents of an examination by radiation imaging,
wherein the setting unit sets, based on the examination information, the imaging apparatus from which the imaging information is obtained.

10. The radiation imaging system according to claim 9, wherein the information obtainment unit obtains the examination information by an operation input made by an operator.

11. The radiation imaging system according to claim 9, wherein the information obtainment unit obtains the examination information from an external apparatus.

12. A radiation imaging system that includes a plurality of imaging apparatuses which are arranged in one imaging room and are configured to generate images based on radiation emitted from radiation generating apparatuses, and a control apparatus configured to communicate with the plurality of imaging apparatuses, the radiation imaging system comprising:
one or more processors; and
a memory including instructions stored thereon that, when executed by the one or more processors, cause the radiation imaging system to function as:
a first selection unit configured to select at least two imaging apparatuses from the plurality of imaging apparatuses arranged in the one imaging room;
an obtainment unit configured to obtain pieces of imaging information of images generated by the at least two imaging apparatuses selected by the first selection unit;
a second selection unit configured to select one imaging apparatus from the at least two imaging apparatuses based on the pieces of imaging information obtained by the obtainment unit; and
an image obtainment unit configured to obtain an image from the imaging apparatus selected by the second selection unit.

13. A control apparatus that communicates with a plurality of imaging apparatuses which are arranged in one imaging room and are configured to generate images based on radiation emitted from radiation generating apparatuses configured to perform radiation irradiation, the control apparatus comprising:
one or more processors; and
a memory including instructions stored thereon that, when executed by the one or more processors, cause the control apparatus to function as:
an obtainment unit configured to obtain imaging information from each of the plurality of imaging apparatuses;
a selection unit configured to select one imaging apparatus from the plurality of imaging apparatuses arranged in the one imaging room based on the imaging information obtained by the obtainment unit;
an image obtainment unit configured to obtain an image from the imaging apparatus selected by the selection unit; and
a setting unit configured to set, from the plurality of imaging apparatuses arranged in the one imaging room, an imaging apparatus from which imaging information is obtained by the obtainment unit.

14. A non-transitory computer readable storage medium storing a computer program for causing a computer to function as each unit included in a control apparatus defined in claim 13.

15. A control apparatus that communicates with a plurality of imaging apparatuses which are arranged in one imaging room and are configured to generate images based on radiation emitted from radiation generating apparatuses, the control apparatus comprising:
one or more processors; and a memory including instructions stored thereon that, when executed by the one or more processors, cause the control apparatus to function as:
a first selection unit configured to select at least two imaging apparatuses from the plurality of imaging apparatuses arranged in the one imaging room;
an obtainment unit configured to obtain pieces of imaging information of images generated by the at least two imaging apparatuses selected by the first selection unit;
a second selection unit configured to select one imaging apparatus from the at least two imaging apparatuses based on the pieces of imaging information obtained by the obtainment unit; and
an image obtainment unit configured to obtain an image from the imaging apparatus selected by the second selection unit.

16. A method of controlling a radiation imaging system that includes a plurality of imaging apparatuses which are arranged in one imaging room and are configured to generate images based on radiation emitted from radiation generating apparatuses configured to perform radiation irradiation and a control apparatus configured to communicate with the plurality of the imaging apparatuses, wherein the method comprises causing the control apparatus to;
obtain imaging information from each of the plurality of imaging apparatuses;
select one imaging apparatus from the plurality of imaging apparatuses based on the obtained imaging information; and
obtain an image from the selected imaging apparatus; and
causing the control apparatus to set, from the plurality of imaging apparatuses arranged in the one imaging room, an imaging apparatus from which imaging information is obtained.

17. A method of controlling a radiation imaging system that includes a plurality of imaging apparatuses which are arranged in one imaging room and are configured to generate images based on radiation emitted from radiation generating apparatuses, and a control apparatus configured to communicate with the plurality of imaging apparatuses, the method comprising:
selecting at least two imaging apparatuses from the plurality of imaging apparatuses arranged in the one imaging room;
obtaining pieces of imaging information of images generated by the selected at least two imaging apparatuses;
selecting one imaging apparatus from the at least two imaging apparatuses based on the obtained pieces of imaging information; and
obtaining an image from the selected imaging apparatus.

* * * * *